(12) United States Patent
Zimmer et al.

(10) Patent No.: US 10,138,836 B2
(45) Date of Patent: Nov. 27, 2018

(54) METHOD AND APPARATUS FOR DETERMINING DIFFERENTIAL DENSITY

(71) Applicant: MICRO MOTION, INC, Boulder, CO (US)

(72) Inventors: Patrick John Zimmer, Denver, CO (US); John Ansdell Houghton, Holmfirth (GB)

(73) Assignee: Micro Motion, Inc., Boulder, CO (US)

( * ) Notice: Subject to any disclaimer, the term of this patent is extended or adjusted under 35 U.S.C. 154(b) by 95 days.

(21) Appl. No.: 15/506,996

(22) PCT Filed: Sep. 18, 2014

(86) PCT No.: PCT/US2014/056229
§ 371 (c)(1),
(2) Date: Feb. 27, 2017

(87) PCT Pub. No.: WO2016/043744
PCT Pub. Date: Mar. 24, 2016

(65) Prior Publication Data
US 2017/0248094 A1 Aug. 31, 2017

(51) Int. Cl.
*G01F 9/02* (2006.01)
*F02D 41/22* (2006.01)
(Continued)

(52) U.S. Cl.
CPC ............. *F02D 41/22* (2013.01); *F02D 41/26* (2013.01); *F02M 37/0064* (2013.01);
(Continued)

(58) Field of Classification Search
CPC ................. G01F 1/8436; G01F 15/022; F02D 2041/224; F02D 2200/0611; F02M 37/0064
(Continued)

(56) References Cited

U.S. PATENT DOCUMENTS

2013/0019669 A1* 1/2013 Wakao ................ F02D 41/0025
73/114.42
2018/0164201 A1* 6/2018 Zimmer .............. F02D 41/0025

FOREIGN PATENT DOCUMENTS

WO 2010056244 A1 5/2010
WO 2011019344 A2 2/2011

* cited by examiner

*Primary Examiner* — Erick Solis
(74) *Attorney, Agent, or Firm* — The Ollila Law Group LLC (57) ABSTRACT

A method for operating an engine system 200 comprising an engine 208 configured to consume a fuel, having at least a two flowmeters 214, 216, is provided. The method includes the step of operating an engine 208 disposed between a supply flowmeter 214 of the at least two flowmeters and a return flowmeter 216 of the at least two flowmeters. A first fuel density in the supply flowmeter 214 and a second fuel density in the return flowmeter 216 are measured. The fuel density measurements 317 between the supply flowmeter 214 and return flowmeter 216 are compared and a differential density measurement value, $\Delta\rho$ 319, based on a difference in the second fuel density and the first fuel density is determined. The $\Delta\rho$ 319 is compared to a range of theoretical differential fuel density values, $\Delta\rho_t$, and potential fuel contamination is indicated if the $\Delta\rho$ lies outside a range of $\Delta\rho_t$ values by a predetermined threshold.

13 Claims, 7 Drawing Sheets

(51) Int. Cl.
    *F02M 37/00*     (2006.01)
    *F02D 41/26*     (2006.01)
    *G01F 1/84*      (2006.01)
    *G01F 15/02*     (2006.01)
    *G01N 9/00*      (2006.01)

(52) U.S. Cl.
    CPC .......... *G01F 1/8436* (2013.01); *G01F 15/022* (2013.01); *F02D 2041/224* (2013.01); *F02D 2200/0606* (2013.01); *F02D 2200/0611* (2013.01); *F02D 2200/0625* (2013.01); *G01N 2009/006* (2013.01); *Y02T 10/40* (2013.01)

(58) Field of Classification Search
    USPC ...................................... 701/103; 123/114.42
    See application file for complete search history.

METHOD AND APPARATUS FOR DETERMINING DIFFERENTIAL DENSITY

TECHNICAL FIELD

The present invention relates to flowmeters, and more particularly to a method and apparatus for determining fuel quality and system efficiency through differential density measurements.

BACKGROUND OF THE INVENTION

Vibrating sensors, such as for example, vibrating densitometers and Coriolis flowmeters are generally known, and are used to measure mass flow and other information related to materials flowing through a conduit in the flowmeter. Exemplary Coriolis flowmeters are disclosed in U.S. Pat. No. 4,109,524, U.S. Pat. No. 4,491,025, and Re. 31,450, all to J. E. Smith et al. These flowmeters have one or more conduits of a straight or curved configuration. Each conduit configuration in a Coriolis mass flowmeter, for example, has a set of natural vibration modes, which may be of simple bending, torsional, or coupled type. Each conduit can be driven to oscillate at a preferred mode.

Some types of mass flowmeters, especially Coriolis flowmeters, are capable of being operated in a manner that performs a direct measurement of density to provide volumetric information through the quotient of mass over density. See, e.g., U.S. Pat. No. 4,872,351 to Ruesch for a net oil computer that uses a Coriolis flowmeter to measure the density of an unknown multiphase fluid. U.S. Pat. No. 5,687,100 to Buttler et al. teaches a Coriolis effect densitometer that corrects the density readings for mass flow rate effects in a mass flowmeter operating as a vibrating tube densitometer.

Material flows into the flowmeter from a connected pipeline on the inlet side of the flowmeter, is directed through the conduit(s), and exits the flowmeter through the outlet side of the flowmeter. The natural vibration modes of the vibrating system are defined in part by the combined mass of the conduits and the material flowing within the conduits.

When there is no flow through the flowmeter, a driving force applied to the conduit(s) causes all points along the conduit(s) to oscillate with identical phase or with a small "zero offset", which is a time delay measured at zero flow. As material begins to flow through the flowmeter, Coriolis forces cause each point along the conduit(s) to have a different phase. For example, the phase at the inlet end of the flowmeter lags the phase at the centralized driver position, while the phase at the outlet leads the phase at the centralized driver position. Pickoffs on the conduit(s) produce sinusoidal signals representative of the motion of the conduit(s). Signals output from the pickoffs are processed to determine the time delay between the pickoffs. The time delay between the two or more pickoffs is proportional to the mass flow rate of material flowing through the conduit(s).

Meter electronics connected to the driver generate a drive signal to operate the driver and also to determine a mass flow rate and/or other properties of a process material from signals received from the pickoffs. The driver may comprise one of many well known arrangements; however, a magnet and an opposing drive coil have received great success in the flowmeter industry. An alternating current is passed to the drive coil for vibrating the conduit(s) at a desired flow tube amplitude and frequency. It is also known in the art to provide the pickoffs as a magnet and coil arrangement very similar to the driver arrangement. However, while the driver receives a current which induces a motion, the pickoffs can use the motion provided by the driver to induce a voltage. The magnitude of the time delay measured by the pickoffs is very small; often measured in nanoseconds. Therefore, it is necessary to have the transducer output be very accurate.

Generally, a flowmeter can be initially calibrated and a flow calibration factor along with a zero offset can be generated. In use, the flow calibration factor can be multiplied by the time delay measured by the pickoffs minus the zero offset to generate a mass flow rate. In most situations, the flowmeter is initially calibrated, typically by the manufacturer, and assumed to provide accurate measurements without subsequent calibrations required. In addition, a prior art approach involves a user zero-calibrating the flowmeter after installation by stopping flow, closing valves, and therefore providing the meter a zero flow rate reference at process conditions.

Vibrating sensors, including Coriolis flowmeters, are often employed in large engine systems, such as those found in marine vessels. For such vessels, proper fuel management is critical for efficient engine system operation. Fuel management typically begins with the bunkering, or fuel loading, at port. It is at this point where fuel is loaded onto the vessel and the quantity is measured. Fuel quality, however, is not known at this time. Fuel quality is determined by sending samples to a laboratory where viscosity, density, and composition may be determined. Unfortunately, this process often takes several days, so fuel quality issues that arise are typically only uncovered after the vessel has left port and is well underway at sea. Additionally, even if fuel quality meets a given set of standards, problems within a fuel system can introduce contaminants, such as water, into the fuel system, which is problematic.

Therefore, there is a need in the art for a method and related apparatus to determine qualitative fuel attributes. There is a need for a method and related apparatus to determine fuel density before entering and after exiting an engine. There is a need to detect potential water content of the fuel. The present invention overcomes these and other problems and an advance in the art is achieved.

SUMMARY OF THE INVENTION

A method for operating an engine system comprising an engine configured to consume a fuel and having at least two flowmeters is provided according to an embodiment. The embodiment comprises the steps of: operating an engine disposed between a supply flowmeter of the at least two flowmeters and a return flowmeter of the at least two flowmeters; measuring a first fuel density in the supply flowmeter and a second fuel density in the return flowmeter; comparing fuel density measurements between the supply flowmeter and return flowmeter; determining a differential density measurement value, $\Delta\rho$, based on a difference between the second fuel density and the first fuel density; comparing the $\Delta\rho$ with a range of theoretical differential fuel density values, $\Delta\rho_t$; and indicating potential fuel contamination if the $\Delta\rho$ lies outside a range of $\Delta\rho_t$ values by a predetermined threshold.

A meter electronics for flowmeters, including a processing system, connected to a system having an engine is provided according to an embodiment. The embodiment is configured to: receive sensor signals from both a supply flowmeter and return flowmeter; determine a differential density measurement value, $\Delta\rho$, between the supply flowmeter and the return flowmeter based on the received sensor signals; compare the $\Delta\rho$ with a range of theoretical differential fuel density values, $\Delta\rho_t$; and store a comparison of the $\Delta\rho$ with the range of $\Delta\rho_t$ values in meter electronics.

ASPECTS

According to an aspect, a method for operating an engine system comprising an engine configured to consume a fuel and having at least two flowmeters is provided. The aspect comprises the steps of: operating an engine disposed between a supply flowmeter of the at least two flowmeters and a return flowmeter of the at least two flowmeters; measuring a first fuel density in the supply flowmeter and a second fuel density in the return flowmeter; comparing fuel density measurements between the supply flowmeter and return flowmeter; determining a differential density measurement value, $\Delta\rho$, based on a difference between the second fuel density and the first fuel density; comparing the $\Delta\rho$ with a range of theoretical differential fuel density values, $\Delta\rho_t$; and indicating potential fuel contamination if the $\Delta\rho$ lies outside a range of $\Delta\rho_t$ values by a predetermined threshold.

Preferably, the method comprises the step of storing the $\Delta\rho$ in a meter electronics.

Preferably, the step indicating potential fuel contamination if the $\Delta\rho$ lies outside a $\Delta\rho_t$ range by a predetermined threshold comprises indicating water contamination of the fuel if the $\Delta\rho$ exceeds the $\Delta\rho_t$ range by a predetermined threshold.

Preferably, the method comprises the steps of receiving a temperature sensor signal value from the supply flowmeter; receiving a temperature sensor signal value from the return flowmeter; and adjusting the first fuel density measurement and the second fuel density measurement to compensate for a temperature of the supply flowmeter and the return flowmeter, respectively.

Preferably, the method comprises the steps of receiving a temperature sensor signal value from a temperature sensor external to the supply flowmeter and the return flowmeter; and adjusting the first fuel density measurement and the second fuel density measurement to compensate for the temperature sensor signal value.

Preferably, the method comprises the step of triggering an alarm if the $\Delta\rho$ lies outside a $\Delta\rho_t$ range by a predetermined threshold.

Preferably, the method comprises the steps of measuring a fuel flow in the supply flowmeter and a fuel flow in the return flowmeter while the engine is operating; calculating engine fuel consumption by comparing fuel flow in the return flowmeter with fuel flow in the supply flowmeter; and indicating a fuel consumption measurement.

According to an aspect, a meter electronics for flowmeters, including a processing system, connected to a system having an engine is provided. The meter electronics is configured to receive sensor signals from both a supply flowmeter and return flowmeter; determine a differential density measurement value, $\Delta\rho$, between the supply flowmeter and the return flowmeter based on the received sensor signals; compare the $\Delta\rho$ with a range of theoretical differential fuel density values, $\Delta\rho_t$; and store a comparison of the $\Delta\rho$ with the range of $\Delta\rho_t$ values in meter electronics.

Preferably, the processing system is configured to indicate potential contamination if the $\Delta\rho$ lies outside the range of $\Delta\rho_t$ values by a predetermined threshold.

Preferably, the processing system is configured to indicate potential water contamination if the $\Delta\rho$ exceeds the range of $\Delta\rho_t$ values by a predetermined threshold.

Preferably, the flowmeters are in fluid communication with a water emulsion system.

Preferably, the processing system is configured to: determine the temperature of the supply flowmeter; determine the temperature of the return flowmeter; and output an adjusted fluid consumption measurement that is corrected for the operating temperature.

Preferably, the processing system is configured to: determine a temperature external to the supply flowmeter and the return flowmeter; and output an adjusted fluid consumption measurement that is corrected for the temperature external to the supply flowmeter and the return flowmeter.

DETAILED DESCRIPTION OF THE INVENTION

FIGS. 1-7 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
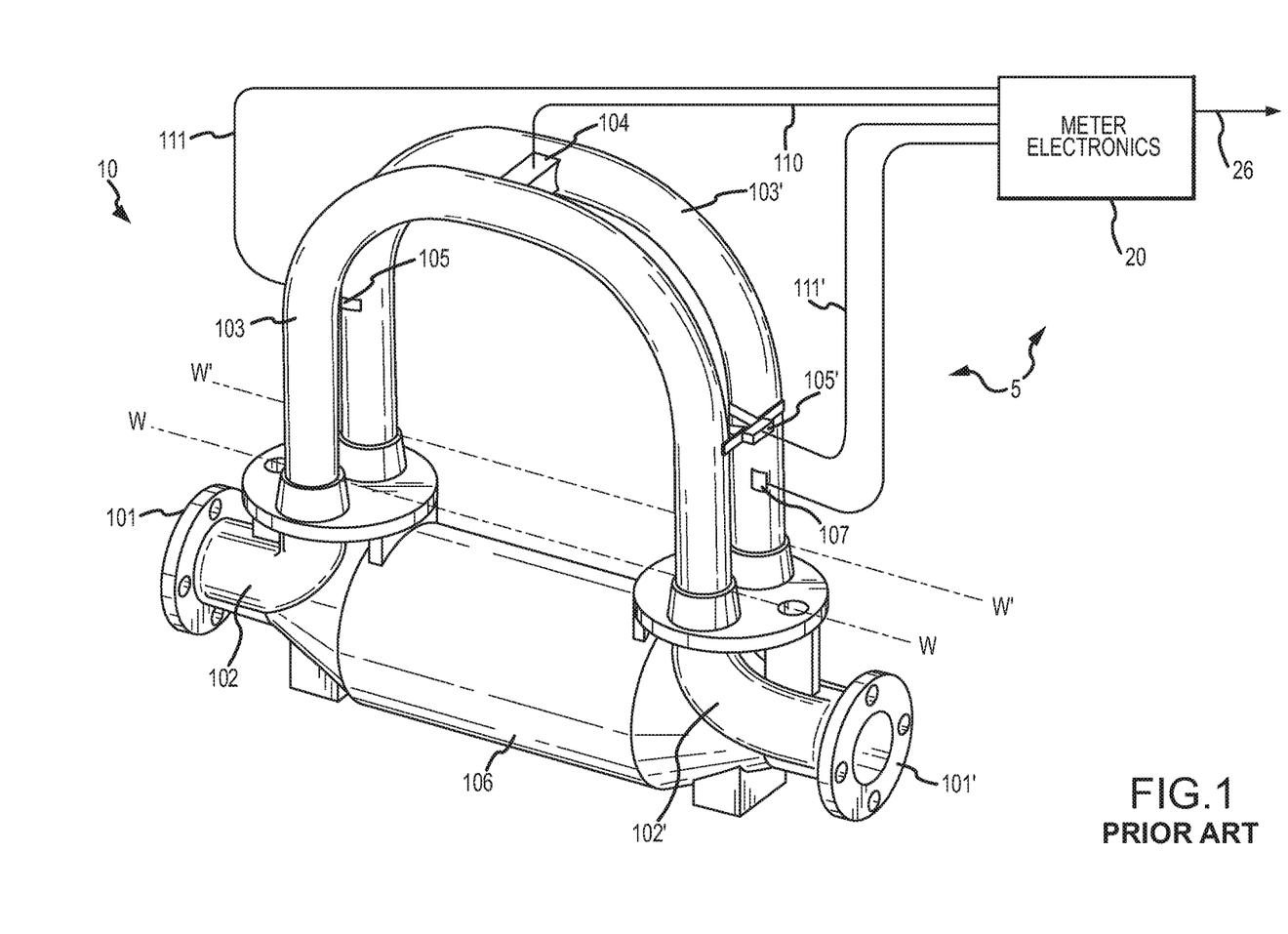
FIG. 1 shows a prior art vibrating sensor assembly.

FIG. 1 illustrates an example of a flowmeter 5 in the form of a Coriolis flowmeter comprising a sensor assembly 10 and one or more meter electronics 20. The one or more meter electronics 20 are connected to sensor assembly 10 to measure a characteristic of a flowing material, such as, for example, density, mass flow rate, volume flow rate, totalized mass flow, temperature, and other information.

The sensor assembly 10 includes a pair of flanges 101 and 101', manifolds 102 and 102', and conduits 103 and 103'. Manifolds 102, 102' are affixed to opposing ends of the conduits 103, 103'. Flanges 101 and 101' of the present example are affixed to manifolds 102 and 102'. Manifolds 102 and 102' of the present example are affixed to opposite ends of spacer 106. The spacer 106 maintains the spacing between manifolds 102 and 102' in the present example to prevent undesired vibrations in conduits 103 and 103'. The conduits 103 and 103' extend outwardly from the manifolds in an essentially parallel fashion. When the sensor assembly 10 is inserted into a pipeline system (not shown) which carries the flowing material, the material enters sensor assembly 10 through flange 101, passes through inlet manifold 102 where the total amount of material is directed to enter conduits 103 and 103', flows through conduits 103 and 103' and back into outlet manifold 102' where it exits the sensor assembly 10 through the flange 101'.

The sensor assembly 10 includes a driver 104. The driver 104 is affixed to conduits 103 and 103' in a position where the driver 104 can vibrate the conduits 103, 103' in the drive mode. More particularly, the driver 104 includes a first driver component (not shown) affixed to conduit 103 and a second driver component (not shown) affixed to conduit 103'. The driver 104 may comprise one of many well known arrangements, such as a magnet mounted to the conduit 103 and an opposing coil mounted to the conduit 103', for example.

In the present example, the drive mode is the first out of phase bending mode and the conduits 103 and 103' are selected and appropriately mounted to inlet manifold 102 and outlet manifold 102' so as to provide a balanced system having substantially the same mass distribution, moments of inertia, and elastic moduli about bending axes W-W and W'-W', respectively. In the present example, where the drive mode is the first out of phase bending mode, the conduits 103 and 103' are driven by the driver 104 in opposite directions about their respective bending axes W-W and W'-W'. A drive signal in the form of an alternating current can be provided by one or more meter electronics 20, such as for example via pathway 110, and passed through the coil to cause both conduits 103, 103' to oscillate. Those of ordinary skill in the art will appreciate that other drive modes may be used within the scope of the present invention.

The sensor assembly 10 shown includes a pair of pickoffs 105, 105' that are affixed to conduits 103, 103'. More particularly, a first pickoff component (not shown) is located on conduit 103 and a second pickoff component (not shown) is located on conduit 103'. In the embodiment depicted, the pickoffs 105, 105' may be electromagnetic detectors, for example—pickoff magnets and pickoff coils that produce pickoff signals that represent the velocity and position of the conduits 103, 103'. For example, the pickoffs 105, 105' may supply pickoff signals to the one or more meter electronics 20 via pathways 111, 111'. Those of ordinary skill in the art will appreciate that the motion of the conduits 103, 103' is proportional to certain characteristics of the flowing material, for example, the mass flow rate and density of the material flowing through the conduits 103, 103'.

It should be appreciated that while the sensor assembly 10 described above comprises a dual flow conduit flowmeter, it is well within the scope of the present invention to implement a single conduit flowmeter. Furthermore, while the flow conduits 103, 103' are shown as comprising a curved flow conduit configuration, the present invention may be implemented with a flowmeter comprising a straight flow conduit configuration. It should also be appreciated that the pickoffs 105, 105' can comprise strain gages, optical sensors, laser sensors, or any other sensor type known in the art. Therefore, the particular embodiment of the sensor assembly 10 described above is merely one example and should in no way limit the scope of the present invention.

In the example shown in FIG. 1, the one or more meter electronics 20 receive the pickoff signals from the pickoffs 105, 105'. Path 26 provides an input and an output means that allows one or more meter electronics 20 to interface with an operator. The one or more meter electronics 20 measure a characteristic of a flowing material, such as, for example, a phase difference, a frequency, a time delay, a density, a mass flow rate, a volume flow rate, a totalized mass flow, a temperature, a meter verification, and other information. More particularly, the one or more meter electronics 20 receives one or more signals, for example, from pickoffs 105, 105' and one or more temperature sensors 107, such as a resistive temperature device (RTD), and use this information to measure a characteristic of a flowing material. The temperature sensors 107 may be with the flowmeters 214, 216 or placed external to the flowmeters 214, 216.

The techniques by which vibrating sensor assemblies, such as for example, Coriolis flowmeters or densitometers measure a characteristic of a flowing material are well understood; therefore, a detailed discussion is omitted for brevity of this description. As a brief overview, however, the density of an unknown fluid flowing through an oscillating flow tube is proportional to the square of the period at which the tube resonates. In U.S. Pat. No. 4,491,009 to Ruesch, a circuit is described that computes density through use of two serially connected integrators. A reference voltage is applied to the first integrator. Inasmuch as the spring constant of each flow tube varies with temperature and thereby changes the resonant frequency, the reference voltage is appropriately compensated for temperature variations of the tube. Both integrators operate for a period of time equivalent to the square of the resonant period. In this manner, the output signal generated by the analog circuit provides a product of a temperature dependent function and the square of the value of the resonant period. With appropriate scaling of the reference voltage, the output analog signal provides a direct readout of the density measurements (in specific gravity units) of the unknown fluid that flows through the flow tube. It should be noted that this is merely one example of a prior art density measurement made with a vibratory meter, and in no way serves to limit the scope of the present invention.

Figure 2:
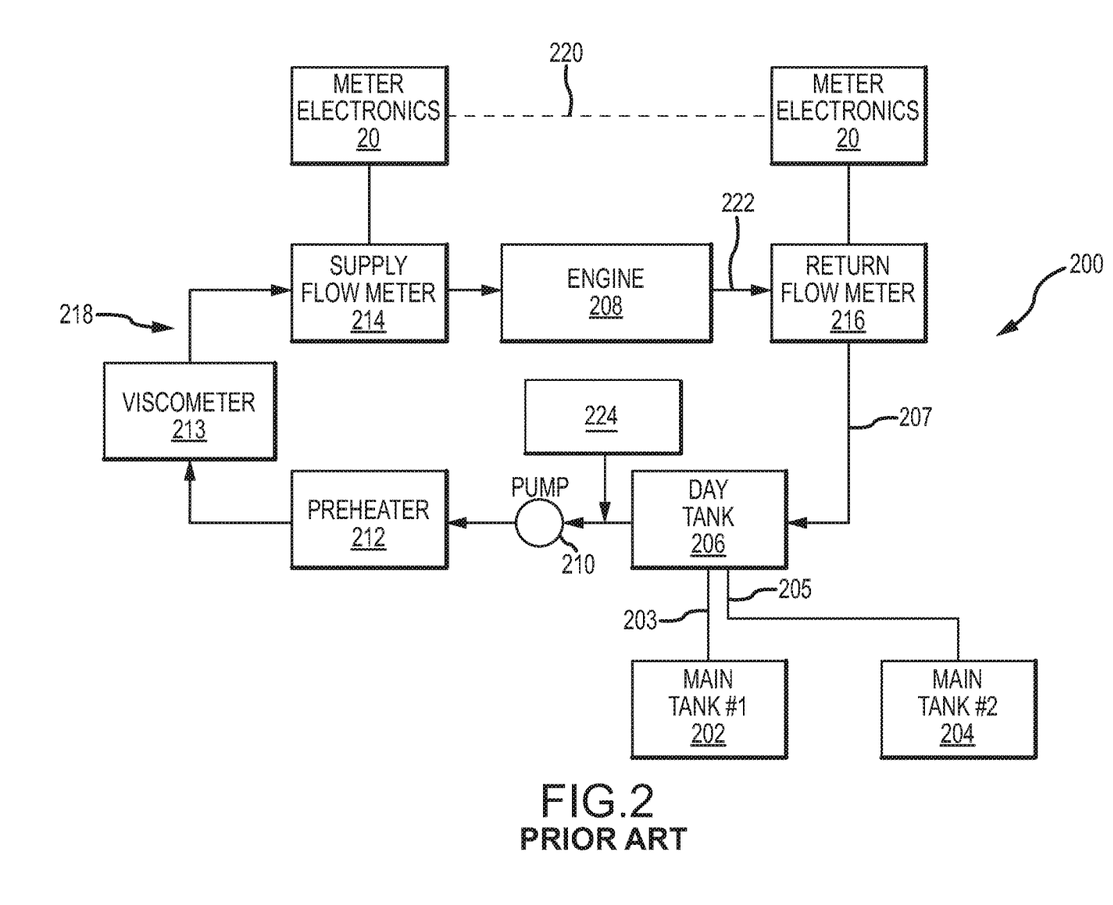
FIG. 2 shows a prior art fuel system.

FIG. 2 illustrates a fuel system 200 according to an embodiment. The system 200 is shown as a typical marine fuel system. Fuel is stored in main tanks 202, 204. In one example of an embodiment, heavy fuel oil (HFO) is stored in a first main tank 202, and marine diesel oil (MDO) is stored in a second main tank 204. The main tanks 202, 204 are fed into a day tank 206 through fuel lines 203 and 205, respectively. This is merely an example, and it should be clear that more than two main tanks may be present, or only one main tank may be present. Additionally, HFO and MDO are merely examples of fuel that may be used, and any fuel is contemplated to be within the scope of the embodiments. The day tank 206 is typically sized to store a limited amount of fuel for safety and contamination purposes. The day tank 206 prevents too much fuel from being stored in an area, such as a ship's engine room, so to minimize fire or explosion risk. Should there be a fire, the limited fuel availability contributes to lower the severity of fire-related incidents. Additionally, the day tank 206 receives fuel that has been presented to an engine 208, but not utilized thereby, thus return fuel is routed back to the day tank 206 through a return fuel line 207. In some systems 200, a water emulsion system 224 may be present to introduce water into the fuel for purposes of reducing emissions.

During operation, fuel is typically recirculated from the day tank 206 to the engine 208 or other fuel consuming device and whatever fuel is not consumed flows back to the day tank 206 in a closed loop circuit 218. Should the day tank 206 become low on fuel, fuel from a main tank 202, 204 replenishes the day tank 206. A pump 210 provides the action necessary to pump the fuel from the day tank 206 to the engine 208 and back. An inline preheater 212 heats the fuel to a temperature that is ideal for the fuel being utilized by the engine 208. For example, the operating temperature of HFO is generally between about 120-150° C., while MDO is ideally around 30-50° C. The appropriate temperature for a particular fuel allows the viscosity of the fuel to be controlled and kept in an ideal range. The kinematic viscosity of the fuel is a measure of the fluidity at a certain temperature. Since the viscosity of a fuel decreases with increasing temperature, the viscosity at the moment the fuel leaves the engine's fuel injectors (not shown) must be within a range dictated by the engine manufacturer in order to create an optimal fuel spray pattern. Viscosities that deviate from specifications lead to substandard combustion, power loss, and potentially deposit formation. The preheater 212, when set correctly for the particular fuel being used, allows for an optimal viscosity to be obtained.

In order to measure flow parameters, such as mass flow rate or density, for example, inline flowmeters are utilized in an embodiment. A supply flowmeter 214 is situated upstream of the engine 208, while a return flowmeter 216 is situated downstream of the engine 208. Since the engine 208 does not use all of the fuel provided to the engine in a common fuel rail system (not shown), for example, excess fuel is recirculated through the day tank 206 and the closed loop circuit 218. Therefore, a single flowmeter would not provide accurate flow measurements, especially as related to engine fuel consumption, thus necessitating both supply 214 and return 216 flowmeters (upstream and downstream of the engine 208, respectively). The difference in flow rates measured by the flowmeters 214, 216 is substantially equal to the flow rate of the fuel being consumed by the engine 208. Therefore, the difference in the measured flow rates between the flowmeters 214, 216 is a predominant value of interest in most applications similar to the configuration shown in FIG. 2. It should be noted, however, that a common rail fuel system serves only as an example, and does not limit the scope of the claimed invention. Other fuel systems wherein fuel is returned and/or recirculated are contemplated. It should also be appreciated that while the system 200 only shows one fuel outlet 222 and two flowmeters 214, 216, in some embodiments, there will be multiple fuel outlets and more than two flowmeters.

When operating large engines, knowing the inlet and outlet condition of the system is critical to fuel system 200 efficiency and performance. Most such systems 200, such as that illustrated in FIG. 2, have a fuel conditioning system, including a preheater 212, that is used to prepare the fuel to a specific viscosity, temperature, and consistency before it enters the engine 208. Having the correct fuel condition can drastically impact the engine's performance. A viscometer 213 downstream of the preheater 212 measures fuel viscosity, and in some embodiments can communicate with the preheater 212 to adjust the preheater temperature such that the fuel remains within a predetermined viscosity range. Currently, fuel monitoring systems nearly exist solely on the inlet side of the engine, and little is done to monitor the fuel's condition after it has been passed through the engine. It has been determined that a change in the fuel's condition after the engine is an indication of the fuel quality or the engine performance.

According to an embodiment, the engine conditions are monitored by examining the density of the fuel before and after the engine 208, as any changes could indicate a potential issue in the system, such as those related to fuel quality and engine performance. The supply flowmeter 214 measures fuel density before the engine 208, and the return flowmeter 216 measures the density of fuel after the engine 208.

Figure 3:
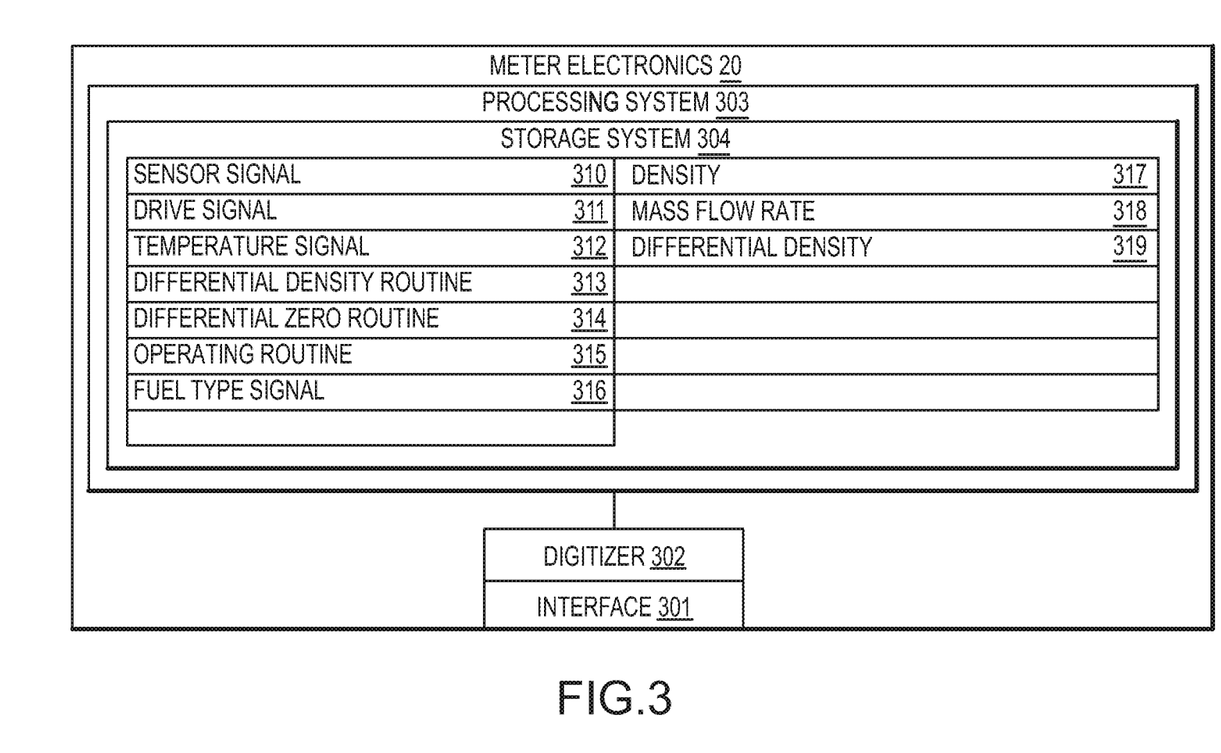
FIG. 3 shows meter electronics according to an embodiment of the invention.

FIG. 3 shows the meter electronics 20 according to an embodiment of the invention. The meter electronics 20 can include an interface 301 and a processing system 303. The processing system 303 may include a storage system 304. The storage system 304 may comprise an internal memory, and/or may comprise an external memory. The meter electronics 20 can generate a drive signal 311 and supply the drive signal 311 to the driver 104. In addition, the meter electronics 20 can receive sensor signals 310 from the flowmeters 214, 216, such as pickoff/velocity sensor signals, strain signals, optical signals, temperature signals, or any other signals known in the art. The meter electronics 20 can operate as a densitometer or can operate as a mass flowmeter, including operating as a Coriolis flowmeter. It should be appreciated that the meter electronics 20 may also operate as some other type of vibrating sensor assembly and the particular examples provided should not limit the scope of the present invention. The meter electronics 20 can process the sensor signals 310 in order to obtain flow characteristics of the material flowing through the flow conduits 103, 103'. In some embodiments, the meter electronics 20 may receive a temperature signal 312 from one or more RTD sensors or other temperature sensors 107, for example.

The interface 301 can receive the sensor signals 310 from the driver 104 or pickoffs 105, 105', via leads 110, 111, 111', respectively. The interface 301 may perform any necessary or desired signal conditioning, such as any manner of formatting, amplification, buffering, etc. Alternatively, some or all of the signal conditioning can be performed in the processing system 303. In addition, the interface 301 can enable communications between the meter electronics 20 and external devices. The interface 301 can be capable of any manner of electronic, optical, or wireless communication.

The interface 301 in one embodiment can include a digitizer 302, wherein the sensor signal comprises an analog sensor signal. The digitizer 302 can sample and digitize the analog sensor signal and produce a digital sensor signal. The digitizer 302 can also perform any needed decimation, wherein the digital sensor signal is decimated in order to reduce the amount of signal processing needed and to reduce the processing time.

The processing system 303 can conduct operations of the meter electronics 20 and process flow measurements from the sensor assembly 10. The processing system 303 can execute one or more processing routines, such as the differential density routine 313, the differential zero routine 314, a general operating routine 315, and fuel type signal routine 316, and thereby process the flow measurements in order to produce one or more flow measurements that are ultimately used to calculate fuel system 200 fuel consumption and calculate differential density measurement value 319, and any other related calculations.

According to an embodiment, the meter electronics 20 can be configured to measure flow through the supply flowmeter 214 and return flowmeter 216 as part of a differential density routine 313. According to an embodiment, the meter electronics 20 can also measure a temperature signal 312, and associate that temperature with the flow rates captured at a given temperature.

As an example of a differential density routine 313, the system 200 may include a supply flowmeter 214 and a return flowmeter 216, that each have (or share) meter electronics 20. The meter electronics, if not shared, may communicate with each other via an interconnect 220. The supply flowmeter 214 and return flowmeter 216 may each generate a density 317. A differential density measurement value, $\Delta\rho$, 319 is calculated using the densities 317 from the supply flowmeter 214 and return flowmeter 216 as part of the differential density routine 313. A mass flow rate 318 or the density 317 may be calculated, for example, as part of the operating routine 315. In one embodiment of the operating routine 315, the return flow rate is subtracted from the supply flow rate, thereby offering a fuel consumption measurement. Meter electronics 20 subtract the two absolute flow signals to produce a differential output, and additionally account for any signal processing delays between the meters.

In an embodiment, the temperature signal 312 is read and a zero-flow rate consumption differential between the return flowmeter 216 and supply flowmeter 214 is also saved and calculated as part of the differential zero routine 314. The differential zero improves the differential flow calculation that is performed between the two meters as it mitigates temperature effects between the meters. This eliminates the need to perform zeroing procedures prior to operation. In a working example, if the engine is off, there is still flow through both flowmeters 214, 216-1000 kg/hr for example. The meters will likely not each read exactly 1000 kg/hr. Instead, one might read 999 kg/hr and the other 1001 kg/hr, so a user would see a 2 kg/hr consumption (or production) measurement when the engine is off. This error of 2 kg/hr would, over long periods of operation, equate to large discrepancies. Therefore, at a particular temperature, a 2 kg/hr differential zero is utilized in the general operating routing 315 as a correction to any flowmeter measurements.

The processing system 303 can comprise a general purpose computer, a micro-processing system, a logic circuit, or some other general purpose or customized processing device. The processing system 303 can be distributed among multiple processing devices. The processing system 303 can include any manner of integral or independent electronic storage medium, such as the storage system 304.

The processing system 303 processes the sensor signal 310 in order to generate the drive signal 311, among other things. The drive signal 311 is supplied to the driver 104 in order to vibrate the associated flow tube(s), such as the flow tubes 103, 103' of FIG. 1.

It should be understood that the meter electronics 20 may include various other components and functions that are generally known in the art. These additional features are omitted from the description and the figures for the purpose of brevity. Therefore, the present invention should not be limited to the specific embodiments shown and discussed.

Figure 4:
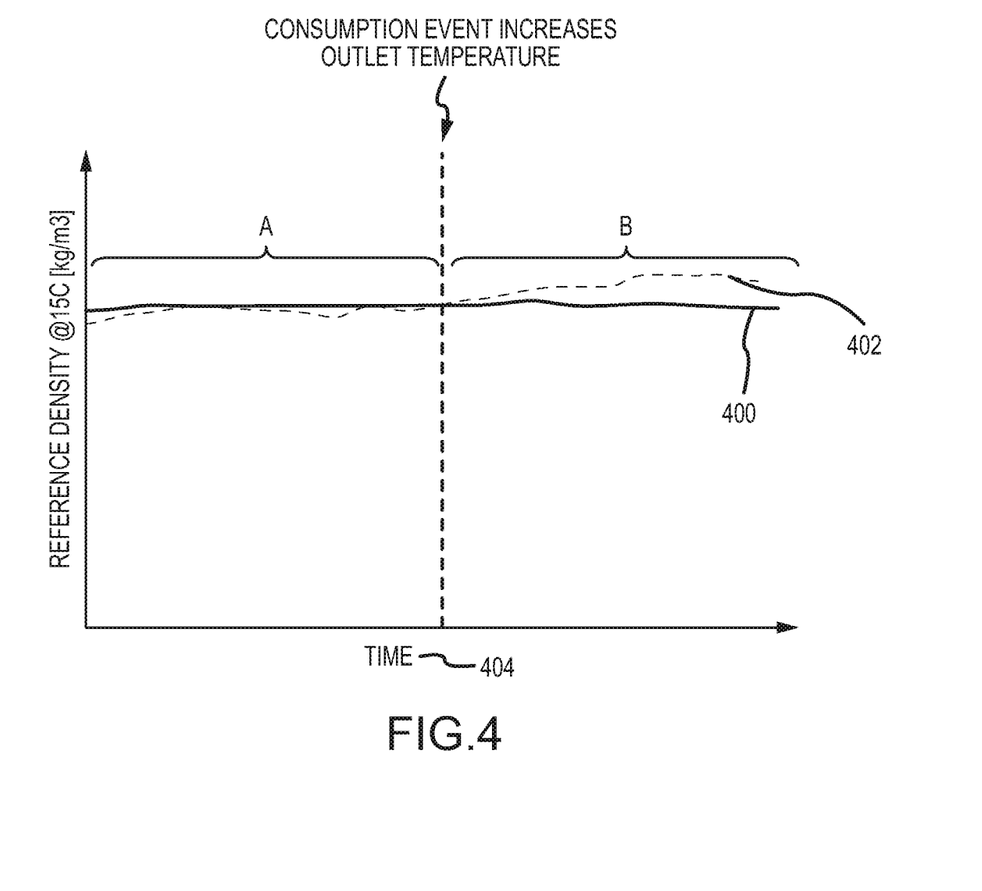
FIG. 4 is a graph illustrating the measured density of fuel in a fuel system according to an embodiment.

FIG. 4 is a graph that describes a differential density measurement. Detecting water contamination of the fuel system is an example, without limitation, of a use of the embodiments presented herein. Besides a general measure of fuel quality, the unexpected presence of water in the fuel supply is a qualitative indicator that a problem may exist. In an embodiment, by examining the differential density measurement (inlet density vs. outlet density), it is possible to determine the potential water content of the fuel entering the engine 208. The density of fuel may be measured by the supply flowmeter 214, and a first fuel density calculated. Once the fuel that is not consumed by the engine 208 passes through the return flowmeter 216, a second density is calculated by the return flowmeter 216. The temperature of the fuel at the engine inlet (and supply flowmeter 214), as a non-limiting example, may be 20° C. cooler than the temperature measured by the return flowmeter 216. Since the density of fuel decreases as a function of increasing temperature, a lower density measurement would be expected in the return flowmeter 216. However, if the density measurement of the return flowmeter 216 is the same or higher than that of the supply flowmeter 214, this indirectly implicates water contamination of the fuel. The graph of FIG. 4 shows the measured inlet density 400 and outlet density 402, as measured by the supply flowmeter 214 and return flowmeter 216, respectively, over time 404. Region A indicates fuel flowing in the closed loop circuit 218 of the fuel system 200 with the engine 208 off. As is apparent, once the engine 208 is running (Region B), the temperature of the outlet will rise. The point where this initiates in the graph is illustrated by the dashed vertical line labeled "Consumption Event Increases Outlet Temperature." In the example provided by this graph, the density measured at the inlet 400 remains stable, even with the engine 208 running. However, the outlet density 402 increases as time passes after the engine 208 is started. This indicates the potential presence of water in the fuel.

In one embodiment, a differential density measurement value, $\Delta\rho$, is calculated according to Equation (1):

$$\Delta\rho = \rho_R - \rho_S \qquad (1)$$

Where:
$\rho_R$=density calculated by return flowmeter; and
$\rho_S$=density calculated by supply flowmeter.
This is merely one example of how a $\Delta\rho$ is calculated, and other methods, equations, and algorithms are contemplated.

In one scenario, if a fuel vendor supplies fuel that contains an amount of water therein that is deemed unacceptably high, a density measurement is useful to elucidate the issue. However, this is a straightforward single-meter density calculation, as the density of the fuel would simply be higher than expected for that particular fuel. It is scenarios where water is entering the fuel system after fuel is bunkered where the differential fuel measurement system 200 is particularly advantageous.

In one embodiment, several water-cooled injectors (not shown) may be employed to atomize and inject fuel into the engine's combustion chamber. Due to the high temperatures found in the combustion chamber, it is often necessary to cool the injector tips that protrude therein. One common scheme by which this is accomplished occurs via circulating water through passages within the injector.

The fuel injector is primarily constructed from a metal (typically steel) body that has fuel supply and return channels therein. The fuel is supplied to an end chamber proximate the injector tip where a valve, such as a needle valve for example without limitation, allows fuel to be metered into the combustion chamber. The valve opens when the fuel pressure exceeds the force of a biasing member configured to keep the valve closed. There may also be passages in the injector body for the supply and return of water to pass to the nozzle. This describes a typical common rail fuel injector system as an example, and does not serve to limit the present invention to such fuel systems. Additionally, though water is described, other coolants are also contemplated. If an injector fails, water may enter the fuel supply. For example, fuel fed to an injector may be presented to the injector at a pressure of 15 psi. The water circulating through the injector may be at 30 psi, for example. In examples of injector failures, should a seal deteriorate, or there be a physical breach of the fuel and water conduits, since the water is circulating at a higher pressure than the fuel within the injector, water will enter the fuel conduits, and contaminate the closed loop circuit 218 of the fuel system 200. This is detectable as a density increase, as measured by the return flowmeter 216 and using the supply flowmeter 214 as a reference.

In a similar example, an engine 208 cylinder head (not shown) can contain water passages so that water may circulate through the cylinder head for cooling purposes. In some engine designs, fuel passages may also be present within the cylinder head. In cases of a cylinder head casting failure or porosity within the casting, it is possible for water to contaminate the fuel supply. As in the above example, in the case of a cylinder head failure, water may enter the fuel conduits and contaminate the closed loop circuit 218 of the fuel system 200. Again, this is detectable as a density increase, as measured by a differential density measurement between the return flowmeter 216 and the supply flowmeter 214.

Nitric oxide (NO) and nitrogen dioxide ($NO_2$) are mononitrogen oxides (Collectively "NOx") that are produced from the reaction of nitrogen and oxygen gases during combustion reaction—most notably at higher temperatures. The large fuel systems 200 of marine vessels serve to create large amounts of nitrogen oxides, which are emitted into the atmosphere and are significant air pollutants. As atmospheric air is approximately 78% nitrogen and 21% oxygen, NOx gases are formed whenever combustion occurs in an engine that is atmospherically aspirated. Unfortunately, NOx gases contribute to the formation of ozone, smog, and potentially acid rain. Therefore, engines and fuel systems often incorporate methods to reduce NOx formation. The addition of water to a marine diesel engine's combustion chamber is a strategy that may be employed to reduce NOx production. This reduces peak combustion temperatures, thus negatively impacting (i.e. reducing) NOx formation. One way to introduce water into the combustion chamber is through the use of emulsified fuels.

An emulsified fuel is typically made from water and a liquid fuel. The emulsion, in the case of fuel systems, is a multi-phase liquid, wherein the water and fuel phases are immiscible. Emulsifiers (or surfactants) are often employed in the emulsion to facilitate a stable mixture. The typical range of water in the fuel is between 5% and 30% by mass. The range varies based upon fuel type, water purity, engine configuration, and other factors beyond the scope of this disclosure. Often the fuel is mixed with the water on-board the ship prior to entering the combustion chamber (See the emulsion system 224 of FIG. 2, for an example). The evaporation of the water in the combustion chamber causes a cooling of the cylinder wall and combustion chamber as a whole. Of course, the lowered combustion temperature results in lowered NOx production. If the percentage of water is too high, engine efficiency suffers, but if the percentage of water in the emulsion is too low, the reduction of NOx compounds is inefficient. Since for a particular engine system the amount of water added to form the water/fuel emulsion is known, the fuel that passes through the return side flowmeter 216 will have an acceptable density range that corresponds with the acceptable volume of water in the emulsion. Should the differential density value indicate that there is no change in fuel density across the engine, this could be indicative of a faulty emulsion system, in that not enough water is being added to the fuel. In a similar vein, should the differential density value be greater than what would be expected based on the volume of water that should be added to the fuel, then this could indicate that too much water is being added to the emulsion.

Figure 5:
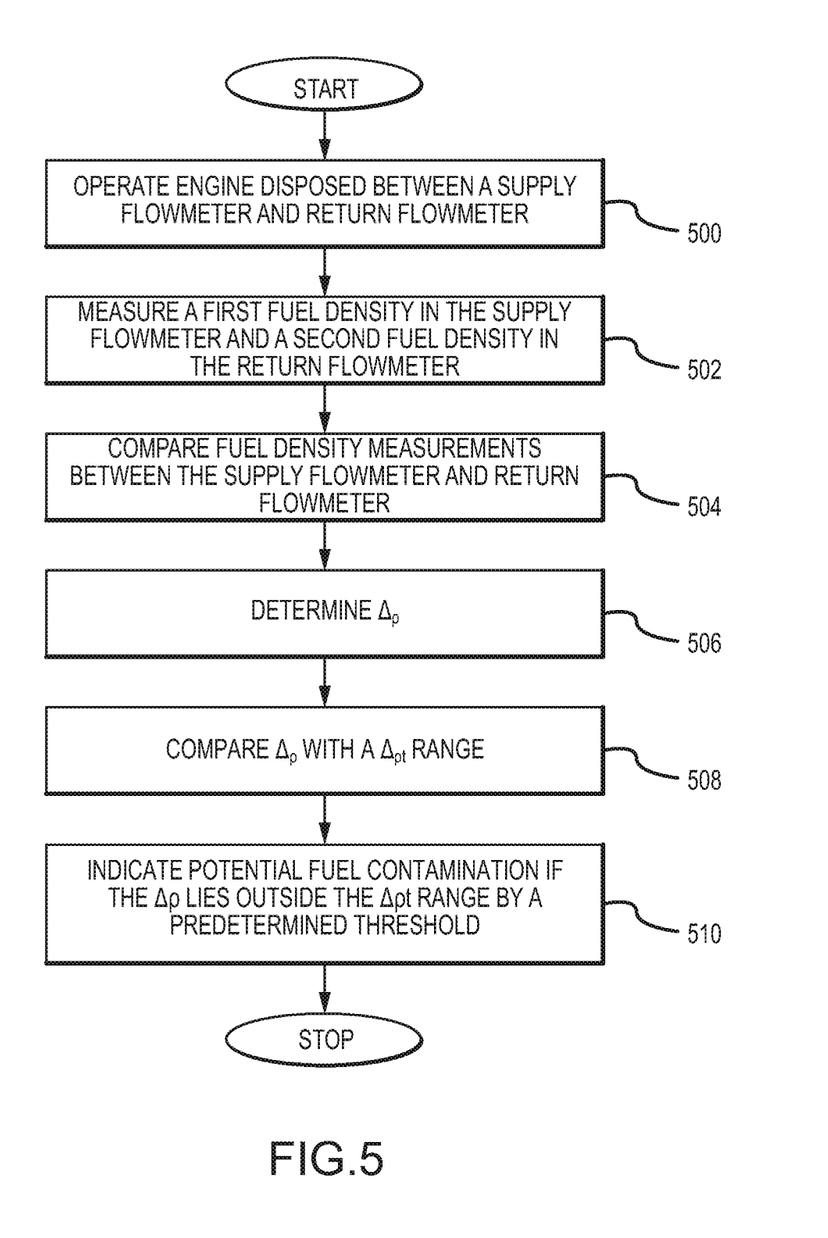
FIG. 5 is a flow chart describing a method of operating an engine system according to an embodiment.

FIG. 5 illustrates an embodiment of a method to indicate potential fuel contamination. A supply flowmeter 214 is situated upstream of the engine 208, and the return flowmeter 216 is situated downstream of the engine 208. In step 500, the engine 208 disposed between the supply flowmeter 214 and return flowmeter 216 is operated. Any difference in flow rates measured by the flowmeters 214, 216 is substantially equal to the flow rate of the fuel being consumed by the engine 208. A first fuel density is measured in the supply flowmeter 214 and a second fuel density is measured in the return flowmeter 216 in step 502. These measured fuel density values are then compared in step 504. As noted above, the density of fuel decreases as a function of temperature, so thus a lower density measurement would be expected in the return flowmeter 216. If the density measurement of the return flowmeter differs from that of the supply flowmeter to a significant extent, this indirectly implicates contamination of the fuel. In step 506 a difference between fuel density values, $\Delta\rho$, is determined, and then compared with a theoretical difference between fuel density value, $\Delta\rho_t$, or range of $\Delta\rho_t$ values, in step 508. The $\Delta\rho$ can be determined using Equation (1), for example without limitation. Other equations, algorithms, and methods are also contemplated, however. Potential fuel contamination is indicated in step 510 if the $\Delta\rho$ lies outside the $\Delta\rho_t$ range by a predetermined threshold. This threshold is dependent on engine type, fuel type, temperature, temperature differentials between flowmeters 214, 216, the presence or absence of a fuel emulsion system 224, etc.

Figure 6:
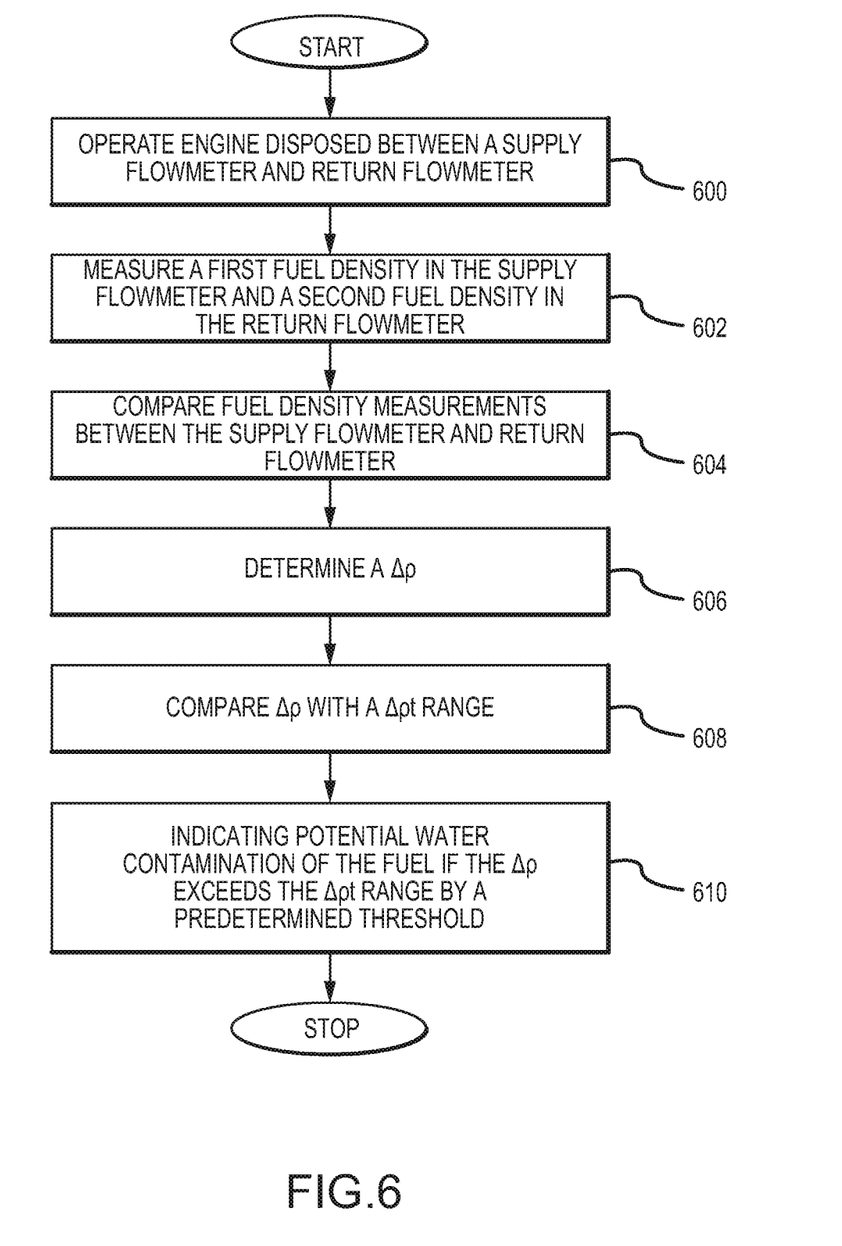
FIG. 6 is flow chart describing another method of operating an engine system according to an embodiment.

As noted above, the temperature of the fuel at the engine inlet (and supply flowmeter 214), is expected to be cooler than the temperature measured by the return flowmeter 216 when the engine 208 is operating. Thus, the density measurement of the return flowmeter 216 should theoretically be lower than that of the supply flowmeter 214. If otherwise, this could indicate that the fuel may be contaminated by water. FIG. 6 is directed to an embodiment for indicating potential water contamination in a fuel system 200. Note that the first five steps illustrated in FIG. 6 are common with the first five steps illustrated in FIG. 5. In step 600, the engine 208 disposed between the supply flowmeter 214 and return flowmeter 216 is operated. A first fuel density is measured in the supply flowmeter 214 and a second fuel density is measured in the return flowmeter 216 in step 602. These measured fuel density values are then compared in step 604. If the density measurement of the return flowmeter differs from that of the supply flowmeter to a significant extent, this indirectly implicates water contamination of the fuel. In step 606 a $\Delta\rho$ is determined, and then compared with a $\Delta\rho t$ or $\Delta\rho t$ range in step 608. In step 610, potential water contamination of the fuel is indicated if the $\Delta\rho$ exceeds the $\Delta\rho_t$ or $\Delta\rho_t$ range by a predetermined threshold. As a non-limiting example application, should water-cooled fuel injectors (not shown) be used to atomize and inject fuel into the engine's combustion chamber, a breach of the injector's water jacket could introduce water into the fuel system after the supply flowmeter 214, but before the return flowmeter 216. This, of course, would contaminate the closed loop circuit 218 of the fuel system 200 with water, which is detectable as a density increase, as measured by the return flowmeter 216 and using the supply flowmeter 214 as a reference.

Figure 7:
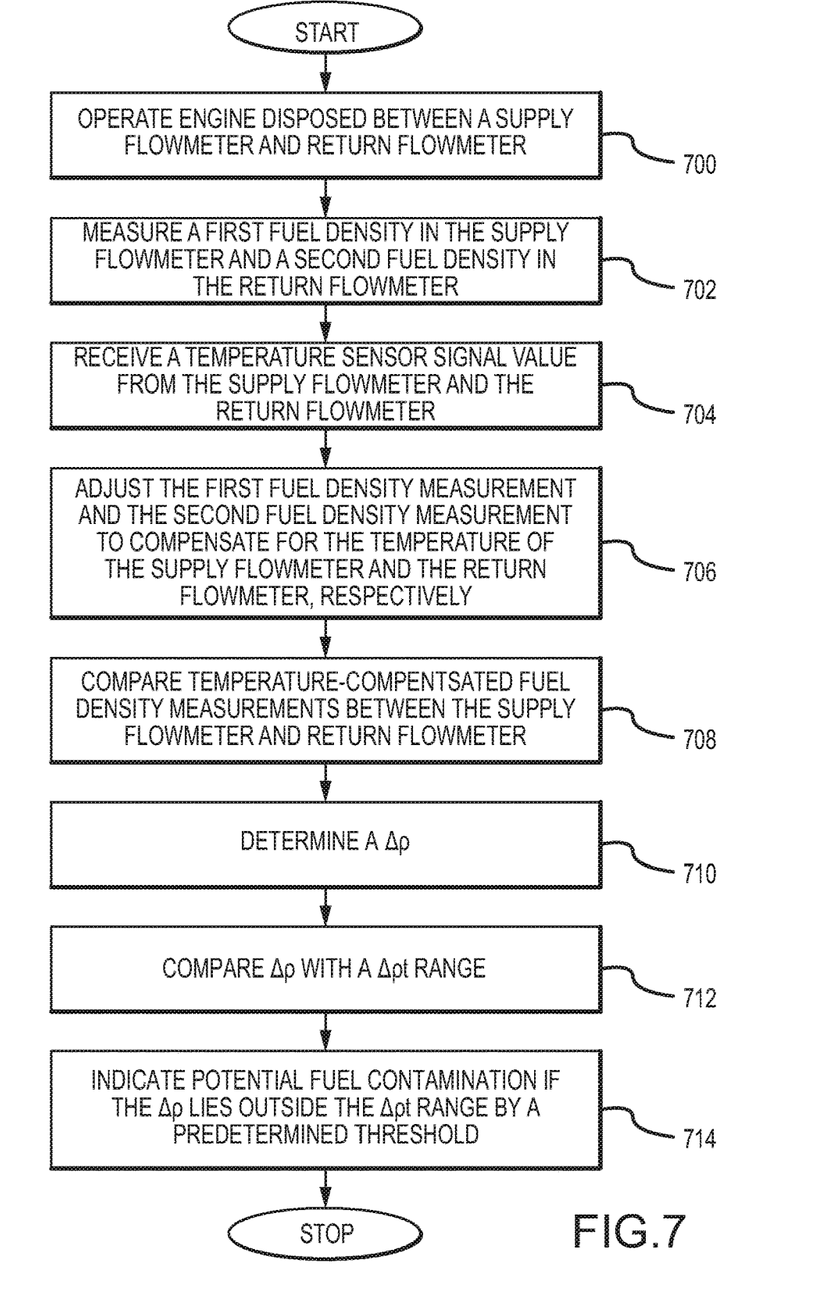
FIG. 7 is a flow chart describing yet another method of operating an engine system according to an embodiment.

FIG. 7 is a related embodiment for indicating potential fuel contamination, wherein the temperature of the flowmeters 214, 216 is utilized. In step 700, the engine 208 disposed between the supply flowmeter 214 and return flowmeter 216 is operated. A first fuel density is measured in the supply flowmeter 214 and a second fuel density is measured in the return flowmeter 216 in step 702. In step 704, temperature sensor signal values are received from both the supply flowmeter 214 and the return flowmeter 216. These values may be stored in meter electronics 20. The temperature may be determined by processing the sensor signals such as those received from a temperature sensor 107. The temperature may be determined using an RTD, for example. The temperature may correspond to a flowmeter temperature, flow tube temperature, flowmeter case temperature, a meter electronics temperature, or a temperature external to the supply or return flowmeters 214, 216 for example. In one embodiment, each flowmeter 214, 216 comprises separate temperature sensors. In one embodiment, a temperature sensor is placed external to the flowmeters 214, 216. In one embodiment, separate temperatures are determined for each flowmeter 214, 216, and each temperature measured is input into meter electronics 20. In another embodiment, temperatures determined for the first fuel density measurement and the second fuel density measurement are adjusted in step 706 to compensate for the temperature of the supply flowmeter 214 and the return flowmeter 216, respectively. In another embodiment, a temperature external to the supply flowmeter 214 and the return flowmeter 216 is determined, and the first fuel density measurement and the second fuel density measurement are adjusted in step 706 to compensate for this measured temperature. These temperature-compensated measured fuel density values are then compared in step 708. A $\Delta\rho$ is then determined in step 710, using the temperature-compensated fuel density values. In step 712, the $\Delta\rho$ is compared with a $\Delta\rho_t$ range. Potential fuel contamination is indicated if the $\Delta\rho$ lies outside the $\Delta\rho_t$ range by a predetermined threshold, as shown in step 714.

In embodiments of methods indicating potential fuel contamination, an alarm may be triggered if the $\Delta\rho$ differs from a $\Delta\rho_t$ or lies outside a $\Delta\rho_t$ range by a predetermined threshold. Additionally, methods may also comprise the steps of measuring the fuel flow in the supply flowmeter and a fuel flow in the return flowmeter while the engine is operating in order to calculate engine fuel consumption by comparing fuel flow in the return flowmeter with fuel flow in the supply flowmeter. The fuel consumption measurement is then indicated.

The present invention as described above provides various systems and methods related to the determination of fuel quality using vibrating flowmeters, such as a Coriolis flowmeter. Although the various embodiments described above are directed towards flowmeters, specifically Coriolis flowmeters, it should be appreciated that the present invention should not be limited to Coriolis flowmeters, but rather the methods described herein may be utilized with other types of flowmeters, or other vibrating sensors that lack some of the measurement capabilities of Coriolis flowmeters.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other vibrating sensors, and not just to the embodiments described above and shown in the accompanying figures. Accordingly, the scope of the invention should be determined from the following claims.

We claim:

1. A method for operating an engine system comprising an engine configured to consume a fuel and having at least two flowmeters, comprising the steps of:
   operating an engine disposed between a supply flowmeter of the at least two flowmeters and a return flowmeter of the at least two flowmeters;
   measuring a first fuel density in the supply flowmeter and a second fuel density in the return flowmeter;
   comparing fuel density measurements between the supply flowmeter and return flowmeter;
   determining a differential density measurement value, $\Delta\rho$, based on a difference between the second fuel density and the first fuel density;
   comparing the $\Delta\rho$ with a range of theoretical differential fuel density values, $\Delta\rho_t$; and
   indicating potential fuel contamination if the $\Delta\rho$ lies outside a range of $\Delta\rho_t$ values by a predetermined threshold.

2. The method for operating the engine system of claim 1, comprising the step of storing the $\Delta\rho$ in a meter electronics.

3. The method for operating the engine system of claim 1, wherein the step indicating potential fuel contamination if the $\Delta\rho$ lies outside a $\Delta\rho_t$ range by a predetermined threshold comprises indicating water contamination of the fuel if the $\Delta\rho$ exceeds the $\Delta\rho_t$ range by a predetermined threshold.

4. The method for operating the engine system of claim 1, comprising the steps of:
   receiving a temperature sensor signal value from the supply flowmeter;
   receiving a temperature sensor signal value from the return flowmeter; and
   adjusting the first fuel density measurement and the second fuel density measurement to compensate for a temperature of the supply flowmeter and the return flowmeter, respectively.

5. The method for operating the engine system of claim 1, comprising the steps of:
   receiving a temperature sensor signal value from a temperature sensor external to the supply flowmeter and the return flowmeter; and
   adjusting the first fuel density measurement and the second fuel density measurement to compensate for the temperature sensor signal value.

6. The method for operating the engine system of claim 1, comprising the step of:
   triggering an alarm if the $\Delta\rho$ lies outside a $\Delta\rho_t$ range by a predetermined threshold.

7. The method for operating the engine system of claim 1, comprising the steps of:
   measuring a fuel flow in the supply flowmeter and a fuel flow in the return flowmeter while the engine is operating;
   calculating engine fuel consumption by comparing fuel flow in the return flowmeter with fuel flow in the supply flowmeter; and
   indicating a fuel consumption measurement.

8. A meter electronics (20) for flowmeters (214, 216), including a processing system (303), connected to a system (200) having an engine (208) configured to:
   receive sensor signals (310) from both a supply flowmeter (214) and return flowmeter (216);
   determine a differential density measurement value, $\Delta\rho$, between the supply flowmeter (214) and the return flowmeter (216) based on the received sensor signals (310);

compare the $\Delta\rho$ with a range of theoretical differential fuel density values, $\Delta\rho_t$; and store a comparison of the $\Delta\rho$ with the range of $\Delta\rho_t$ values in meter electronics (20).

9. The meter electronics (20) for flowmeters (214, 216) of claim 8, wherein the processing system (303) is configured to indicate potential contamination if the $\Delta\rho$ lies outside the range of $\Delta\rho_t$ values by a predetermined threshold.

10. The meter electronics (20) for flowmeters (214, 216) of claim 8, wherein the processing system (303) is configured to indicate potential water contamination if the $\Delta\rho$ exceeds the range of $\Delta\rho_t$ values by a predetermined threshold.

11. The meter electronics (20) for flowmeters (214, 216) of claim 8, wherein the flowmeters (214, 216) are in fluid communication with a water emulsion system (224).

12. The meter electronics (20) for flowmeters (214, 216) of claim 8, wherein the processing system (303) is configured to:

determine the temperature of the supply flowmeter (214);

determine the temperature of the return flowmeter (216); and output an adjusted fluid consumption measurement that is corrected for the operating temperature.

13. The meter electronics (20) for flowmeters (214, 216) of claim 8, wherein the processing system (303) is configured to:

determine a temperature external to the supply flowmeter (214) and the return flowmeter (216); and output an adjusted fluid consumption measurement that is corrected for the temperature external to the supply flowmeter (214) and the return flowmeter (216).

\* \* \* \* \*